United States Patent [19]

Williamitis et al.

[11] Patent Number: 4,664,657
[45] Date of Patent: May 12, 1987

[54] LUBRICANT FOR CATHETER ASSEMBLIES EMPLOYING THERMOPLASTIC CATHETERS

[75] Inventors: Victor A. Williamitis, Dayton; Charles W. McGary, Centerville, both of Ohio

[73] Assignee: Becton, Dickinson and Company, Franklin Lakes, N.J.

[21] Appl. No.: 746,150

[22] Filed: Jun. 18, 1985

[51] Int. Cl.$^4$ .............................................. A61M 5/325
[52] U.S. Cl. .................................... 604/265; 428/450
[58] Field of Search ............................. 604/164–167, 604/172, 264, 265; 428/450

[56] References Cited

U.S. PATENT DOCUMENTS 3,574,673  4/1971  Schweiger ........................... 117/132
4,534,363  8/1985  Gold .................................... 604/265
4,582,762  4/1986  Onohara et al. ..................... 604/265
4,588,398  5/1986  Daugherty et al. ................. 604/265

OTHER PUBLICATIONS

Dow Corning Bulletin 51-374B—May, 1982 "Dow Corning 360 Medical Fluid".
Dow Corning Bulletin 51-599—Jul., 1982 "Dow Corning MDX4-4159 Fluid".

*Primary Examiner*—John D. Yasko
*Attorney, Agent, or Firm*—Robert P. Grindle

[57] ABSTRACT

A lubricating film for preventing time-temperature dependent increase in adhesion in a catheter assembly including an interference-fitted thermoplastic catheter wherein a film of polydimethylsiloxane is deposited on the tip of the cannula, preferably from a solution of a volatile solvent.

11 Claims, 1 Drawing Figure

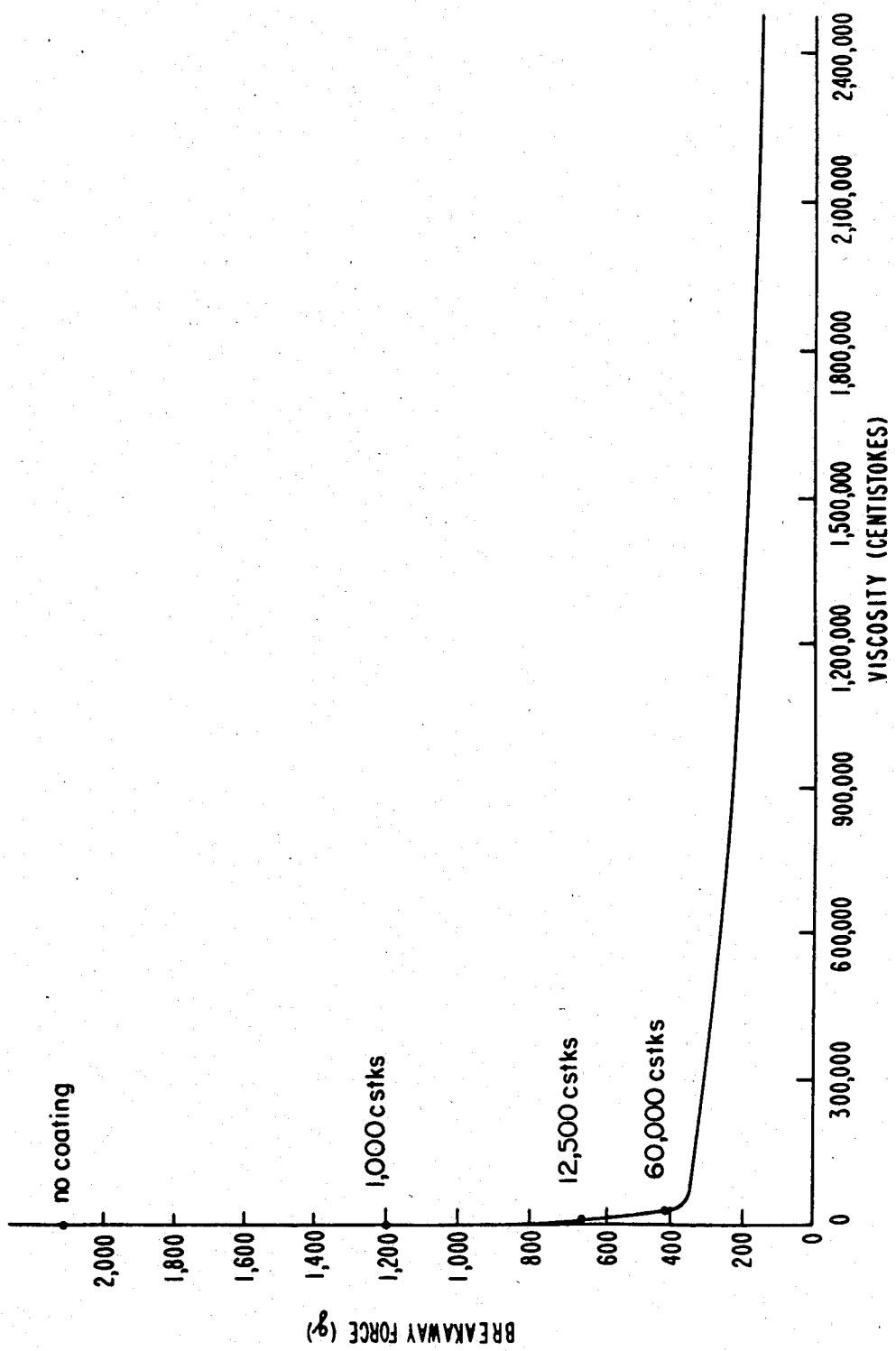

LUBRICANT FOR CATHETER ASSEMBLIES EMPLOYING THERMOPLASTIC CATHETERS

BACKGROUND OF THE INVENTION

The present invention relates to a lubricant which is useful in catheter-cannula assemblies. More particularly, the present invention relates to a lubricant which is useful in preventing time-temperature dependent increase in adhesion, which has been observed in some catheter assemblies in which a thermoplastic catheter is carried on the cannula with an interference fit between the tip of the catheter and the cannula. Still more particularly, the present invention relates to a lubricant useful with interference-fitted polyurethane catheters.

Catheter assemblies in which the catheter is formed from a thermoplastic polymer, in some cases, have been designed with an interference fit between the tip of the catheter and the cannula to facilitate skin and vein penetration and prevent catheter pull-back (i.e., the catheter pulling back or spreading on the cannula during insertion). Typically the interference fit is about 0.025 to 0.0625 mm (about 0.001 to 0.0025 inch).

Upon storage of interference fitted thermoplastic catheter assemblies for long periods of time or at elevated temperatures an excessive amount of adhesion develops between the catheter tip and the cannula. The catheter tends to soften and adhere to the surface of the cannula. Such high adhesion levels can develop that, after storage, the thermoplastic catheter is extremely difficult to remove from the cannula. In some cases, the adhesion is so great that the catheter cannot be removed without deformation. In any event, the catheter becomes so adhered to the cannula that it cannot be removed without causing significant additional discomfort or pain to the patient.

While it is known in the art to lubricate the cannula to facilitate insertion and removal of the catheter, previous lubricants have been less effective in preventing the aforementioned time-temperature dependent increase in adhesion. In particular, the organosiloxanes described in U.S. Pat. No. 3,574,673, such as Dow Corning MDX4-4159 Fluid, have been used as lubricants for hypodermic needles to provide needle point lubrication for skin and vein penetration. These organosiloxanes are copolymers of dimethylsiloxane and aminoalkylsiloxanes and moisture cure to a relatively soft and gelatinous film. These organosiloxanes are referred to as gelling siloxanes and, depending on ambient humidity, they require several days to fully cure. When they are applied to a hypodermic needle, partially cured, and inserted into an interference-fitting catheter, in the conventional manner, the silicone film is largely wiped up the needle and accumulates in a visible ring above the tip of the needle. This limits use of this material to very light coatings which will not accumulate in a ring. The very thin film which remains between the catheter tip and cannula does not effectively prevent the time-temperature dependent increase in adhesion. Thus, a significant disadvantage of gelling siloxanes is that a minimum of several hours is required to partially cure the coating before the cannula can be assembled with the catheter and heavier coatings which would be more effective in adhesion control cannot be used.

SUMMARY OF THE INVENTION

The present invention relates to catheter assemblies in which a thin coating of polydimethylsiloxane is applied to at least the distal end of a cannula to facilitate skin and vein penetration and to prevent adhesion between the tip of the catheter and the cannula from building to levels at which a thermoplastic catheter cannot be removed from the cannula without causing significant additional pain to the patient.

It has been found that higher viscosity polydimethylsiloxane coatings can be applied to a cannula in significantly higher coating weights than gelling siloxanes without being wiped up the needle to the extent of a gelling siloxane when inserted into an interference-fitted catheter. As a consequence, an effective, lubricative release coating remains between the tip of the catheter and the cannula which controls adhesion.

The release coating of the present invention is advantageous because it reduces adhesion and, more particularly, time-temperature dependent increase in adhesion upon storage, and facilitates skin and vein penetration. The coating is also advantageous because it can be set quickly (typically in 10 to 20 seconds) by simply flashing off a volatile solvent from the polydimethylsiloxane.

Another important advantage of the coating is that it provides a consistent, reproducible level of adhesion, (regardless of storage conditions) between the catheter and cannula. With other coatings there is wide variation in the level of adhesion. This makes the catheter assembly inconvenient to use since the user never knows how much force is required to remove the catheter from the cannula. In the present invention, a consistent level of adhesion is achieved and, as such, the user readily develops a feel for how much force is required to remove the catheter.

A principal object of the present invention is to provide a lubricant for use in thermoplastic catheter assemblies which prevents the development of excessive catheter tip-to-needle adhesion upon storage and provides effective needle point lubrication for skin and vein penetration.

A further object of the present invention is to provide a lubricant for a thermoplastic catheter assembly which provides a consistant, reproducible level of adhesion between the catheter and the cannula.

A still further object of the present invention is to provide a lubricative film for thermoplastic catheter assemblies which can be quickly set by simply flashing off a solvent.

Another object of the present invention is to provide a lubricant for polyurethane catheter assemblies.

These and other objectives are achieved in accordance with the present invention which, in one embodiment provides:

A catheter assembly comprising a cannula, a catheter formed from a thermoplastic polymer and carried on the cannula in an interference fit, and a coating of a polydimethylsiloxane having a viscosity in the range of about 60,000 to 2,500,000 centistokes on the surface of the cannula and in contact with the catheter.

In accordance with a preferred embodiment of the invention, the catheter is formed from polyurethane; the polydimethylsiloxane has a viscosity in the range of about 600,000 to about 2,500,000 centistokes, and the polydimethylsiloxane is applied to the surface of the cannula in an amount of about 60 to 100 μg/cm for a 16 gauge cannula and in an amount proportional thereto based on surface area for larger or smaller cannulas.

Another embodiment of the invention is a method for controlling adhesion between a cannula and a thermoplastic catheter carried on the cannula in an interference fit which comprises immersing at least the distal end of the cannula in a solution of polydimethylsiloxane in a solvent, withdrawing the cannula from the solution, drying the cannula by evaporating the solvent, and inserting the cannula into a catheter formed from a thermoplastic polymer.

BRIEF DESCRIPTION OF THE DRAWING

The FIGURE is a graph showing the relationship between breakaway force (g) and viscosity (centistokes) of polydimethylsiloxane for a polyurethane catheter assembly having an interference fit of 0.076 mm (0.003 inch) after storage for 24 hours at 250° F. (121° C.) wherein the polydimethylsiloxane is carried on the surface of a 16 gauge cannula in an amount of 70 µg/cm.

DETAILED DESCRIPTION

The present invention is useful in controlling adhesion between the catheter tip and the cannula for a variety of thermoplastic catheters including, but not limited to, catheters formed from polyvinyl chloride, polyurethane, and ethylene-chlorotrifluoroethylene copolymer and fluorinated ethylene-propylene copolymer. It is particularly useful, however, with polyurethane catheters.

The polydimethylsiloxanes used in the present invention can be straight chain or branched chain polydimethylsiloxanes provided that they have a viscosity in the range of about 60,000 to 2,500,000 centistokes, and, more preferably, 600,000 to 2,500,000 centistokes (unless otherwise indicated, all viscosities are measured at 23° C.). The effect of viscosity on time-temperature dependent adhesion, as simulated by heating 24 hours at 121° C., is shown in the FIGURE. As can be seen, polydimethylsiloxanes having viscosity less than 60,000 centistokes are less useful. As the viscosity decreases to levels below 60,000, adhesion between the catheter tip and the cannula increases in indirect proportion to the viscosity. It is not shown in the FIGURE, but as the viscosity exceeds 2,500,000 centistokes, the coating begins to loose its effectiveness. Breakaway force increases.

The preferred polydimethylsiloxane is a trimethylsiloxyl-terminated straight chain compound.

In accordance with the present invention, polydimethylsiloxanes are dissolved in a solvent and coated on the cannula by immersing the cannula (preferably only the tip) in the solution and withdrawing it at a controlled rate. The amount of polydimethylsiloxane that can be applied to the surface of a cannula is a function of the concentration of it in the solution, the viscosity of the polydimethylsiloxane, the solvent, and the rate with which the cannula tip is withdrawn from the solution. Higher solution concentration and higher withdrawl rates provide heavier coatings. These conditions are appropriately balanced such that the desired coating amount is applied to the surface of the cannula, preferably with high coating speed.

The polydimethylsiloxane coating is applied to the cannula in an amount sufficient to reduce adhesion. The optimum amount varies with the size of the cannula and the viscosity of the polydimethylsiloxane. As coating amount increases, a limiting minimum level of adhesion (or a limiting maximum reduction in adhesion) is achieved. It is generally unnecessary and undesirable to apply the coating in an amount which provides the lowest level of adhesion since heavier coatings, which increase expense and increase the likelihood that foreign material will enter the blood stream, are required. As a general rule, the minimum amount of coating required to provide about 90 to 95% of the maximum reduction in adhesion is used.

Studies have shown that for a 16 gauge hypodermic needle, the optimum coating weight ranges from about 60 to 100 µg/cm and, more preferably, from about 70 to 90 µg/cm. For other gauge needles, for example, 14, 18, 22, or 24 gauge, an amount which is proportionately higher or lower, based on the ratio of the surface areas of the needles, is used.

The optimum coating weight also is a function of the viscosity of the polydimethylsiloxane polymer. For a 1,000,000 centistokes material, the optimum coating weight for a 16 gauge catheter is about 70 µg/cm. This amount can be deposited by dipping the tip of the needle in a 4 weight % solution of polydimethylsiloxane in trichlorotrifluoroethane and withdrawing it at a rate of 4 seconds per inch (2.54 cm). For faster production, the same coating can be applied from a 2.4 weight % solution of the polymer and withdrawing it a rate of 10 ft/min (3 m/min).

For maximum production efficiency, the polydimethylsiloxane is dissolved in a volatile solvent such as trichlorotrifluoroethane or a similar halogenated hydrocarbon having a boiling point less than about 60° C. Higher boiling solvents can be used, but longer times would be required to dry the coating on the surface of the needle. One particular advantage of the film of the present invention over gelling siloxanes is that it can be rapidly set by simple drying, as contrasted with the gelling siloxanes which require several hours to cure.

EXAMPLE

A comparison of the adhesion (breakaway) force obtained using a gelling type siloxane (MDX-4-4159 from Dow Chemical Company), polydimethylsiloxanes and no coating was made for a 16 gauge needle after 24 hours at room temperature and 24 hours at 250° F. (121° C.).

Ten needles were coated with each of the coatings shown in the table below. The polydimethylsiloxanes were applied by dipping the needle in a 4% solution of the polydimethylsiloxane in trichlorotrifluoroethane and withdrawing the needle at a rate of 4 seconds per 2.54 cm and allowing the needle to dry 10 to 30 seconds before assembling it with the catheter. The inside diameter of the tip of the catheters was made 0.0625 mm (0.0025 inch) less than the outside diameter of the needles to provide an interference fit. Adhesion (breakaway force) was measured by mounting the catheter assembly in one jaw of an Instrom Tensile Tester, grasping the proximal edge of the catheter with the other jaw, and removing the catheter. The results are shown in the table below.

| Silicone (mg/inch) | Coating Weight (µg/in) | Breakaway Force | |
|---|---|---|---|
| | | 24 H Room Temp. (g)* | 24 H 250° F. (g)* |
| no coating | 0 | 371 ± 171 | 2142 ± 97 |
| gelling siloxane (Dow MDX-4-4159 fluid) | 26 | 178 ± 50 | 337 ± 112 |
| gelling siloxane (Dow MDX-4-4159 fluid) | 26 | 242 ± 49 | 357 ± 51 |
| polydimethylsiloxane (1,000 centistokes) | 200 | 255 ± 30 | 1189 ± 210 |

-continued

| Silicone (mg/inch) | Coating Weight (μg/in) | Breakaway Force | |
|---|---|---|---|
| | | 24 H Room Temp. (g)* | 24 H 250° F. (g)* |
| polydimethylsiloxane (12,500 centistokes) | 200 | 243 ± 27 | 651 ± 151 |
| polydimethylsiloxane (1,000,000 centistokes) | 26 | 190 ± 42 | 418 ± 153 |
| polydimethylsiloxane (1,000,000 centistokes) | 200 | 92 ± 32 | 77 ± 32 |

*one standared deviation of test data

The 24 hour exposure at 250° F. simulates a prolonged exposure at lower temperatures. The data in the table shows that higher viscosity polydimethylsiloxanes can be used in high coating weights to control time-temperature dependent increase in adhesion. After 24 hours at room temperature the higher viscosity (1,000,000 centistokes) polydimethylsiloxane provides a lower breakaway force than is available with the gelling siloxane or the lower viscosity polydimethylsiloxane. Upon storage at the higher temperature, however, the differences in breakaway force are substantially greater showing the effectiveness of the coating of the present invention in preventing time-temperature increase in adhesion.

Having described the invention in detail and by reference to specific embodiments thereof, it will be apparent that numerous modifications and variations are possible without departing from the scope of the invention as defined by the following claims:

What is claimed is:

1. A catheter assembly comprising a cannula, a catheter, and a coating of polydimethylsiloxane on the surface of said cannula, said catheter being formed from a thermoplastic polymer and being carried on said cannula in an interference fit, said coating being present on the surface of said cannula where said cannula contacts said catheter, and said polydimethylsiloxane having a viscosity in the range of about 60,000 to about 2,500,000 centistokes.

2. The catheter assembly of claim 1 wherein said polydimethylsiloxane has a viscosity in the range of about 600,000 to about 2,500,000 centistokes.

3. The catheter assembly of claim 2 wherein said polydimethylsiloxane is applied to said cannula in an amount based on surface area porportional to about 60 to 100 μg/cm for a 16 gauge catheter.

4. The catheter assembly of claim 3 wherein said catheter is formed from a thermoplastic polyurethane.

5. The catheter assembly of claim 4 wherein said polydimethylsiloxane is applied to said cannula in an amount based on surface area proportional to about 70 to 90 μg/cm for a 16 gauge catheter.

6. A method for controlling adhesion between a cannula and a thermoplastic catheter carried on said cannula in an interference fit comprising immersing at least the distal end of said cannula in a solution of polydimethylsiloxane wherein said polydimethylsiloxane has a viscosity in the range of about 60,000 to 2,500,000 centistokes, withdrawing said cannula from said solution, drying said cannula, and inserting said cannula into a catheter formed from a thermoplastic polymer.

7. The method of claim 6 wherein said polydimethylsiloxane has a viscosity in the range of about 600,000 to 2,500,000 centistokes.

8. The method of claim 7 wherein said solution contains about 2 to 4 percent of said polydimethylsiloxane.

9. The method of claim 8 wherein said solution is a solution of polydimethylsiloxane in a solvent having a boiling point less than about 60° C.

10. The method of claim 9 wherein said polydimethylsiloxane is applied to said cannula in an amount proportional to about 60 to 100 μg/cm for a 16 gauge catheter.

11. The method of claim 10 wherein said catheter is formed from a thermoplastic polyurethane.

* * * * *